(12) United States Patent
Zhang et al.

(10) Patent No.: US 9,044,499 B1
(45) Date of Patent: Jun. 2, 2015

(54) NS1/2-DEFICIENT RESPIRATORY SYNCYTIAL VIRUS AND MELANOMA TREATMENT

(76) Inventors: Weidong Zhang, Tampa, FL (US);
Lixian Jiang, Wesley Chapel, FL (US);
Calvin Cao, Tampa, FL (US)

( * ) Notice: Subject to any disclaimer, the term of this patent is extended or adjusted under 35 U.S.C. 154(b) by 0 days.

(21) Appl. No.: 13/134,543

(22) Filed: Jun. 10, 2011

Related U.S. Application Data

(60) Provisional application No. 61/398,236, filed on Jun. 22, 2010.

(51) Int. Cl.
*C12N 15/86* (2006.01)

(52) U.S. Cl.
CPC ..... *A61K 35/768* (2013.01); *C12N 2760/18121* (2013.01); *C12N 2760/18132* (2013.01); *C12N 2760/16122* (2013.01); *C12N 2760/18532* (2013.01)

(58) Field of Classification Search
CPC ............. C12N 15/86; C12N 2770/24143; C12N 2770/24161; C12N 2770/24162; C12N 7/00; C12N 2760/16122; C12N 2760/18121; C12N 2760/18132; C12N 2750/14332; C12N 2760/18532; C12N 2710/10332; C12N 2710/16632; C12N 2710/16662; A61K 35/768; A61K 39/155; C07K 14/005; C07K 14/535; C07K 2319/00; C07K 2319/33; C07K 2319/01
See application file for complete search history.

(56) References Cited

U.S. PATENT DOCUMENTS

| | | | |
|---|---|---|---|
| 6,986,881 B1 | 1/2006 | Livingston et al. | |
| 7,709,007 B2 | 5/2010 | Murphy et al. | |
| 2004/0109877 A1 | 6/2004 | Palese et al. | |
| 2010/0303839 A1* | 12/2010 | Bose et al. | 424/184.1 |

FOREIGN PATENT DOCUMENTS

WO    WO 2008144067    * 11/2006

OTHER PUBLICATIONS

Hao et al. Molecular Cancer Therapeutics, 2007, vol. 6, pp. 2220-2229.*
Mohapatra et al. Molecular Cancer Research 2007, vol. 5, pp. 145-151.*
Spann et al. Journal of Virology, (Apr. 2004) vol. 78, No. 8, pp. 4363-4369.*
Munir et al. Journal of Virology, Sep. 2008, vol. 82,, No. 17, pp. 4363-4369.*
Muster et al. (2004) Int. J. Cancer 110, 15-21.
Restifo et al. (1998) Virology 249, 89-97.
Shayakhmetov et al. (2004) J. Virology 78, 5368-81.
Spann et al. (2004) J. Virology 78, 4363-69.
Munir et al. (2008) J. Virology 82, 8780-96.
Hao et al. (2007) Molecular Cancer Therapeutics 6, 2220-29.
Mohapatra et al. (2007) Molecular Cancer Research 5, 141-151.
Everts et al. (2005) Cancer Gene Therapy, 12, 141-161.
Chattopadhyay et al. (2004) Virus Research, 99, 139-145.
Smallwood et al. (2002) Virology, 304, 135-145.
Tomasinsig et al. (2005) Current Protein and Peptide Science, 6, 23-34.
Skolnick et al. (2000) Trends in Biotech, 18, 34-39.

* cited by examiner

*Primary Examiner* — Bao Li

(57) ABSTRACT

The invention discloses an engineered oncolytic respiratory syncytial virus (RSV), NS1 and NS2 gene deficient RSV (ΔNS1/NS2 RSV), and its usage to treat different types of human melanoma by killing cancer cells with in vitro evidences.

5 Claims, 6 Drawing Sheets

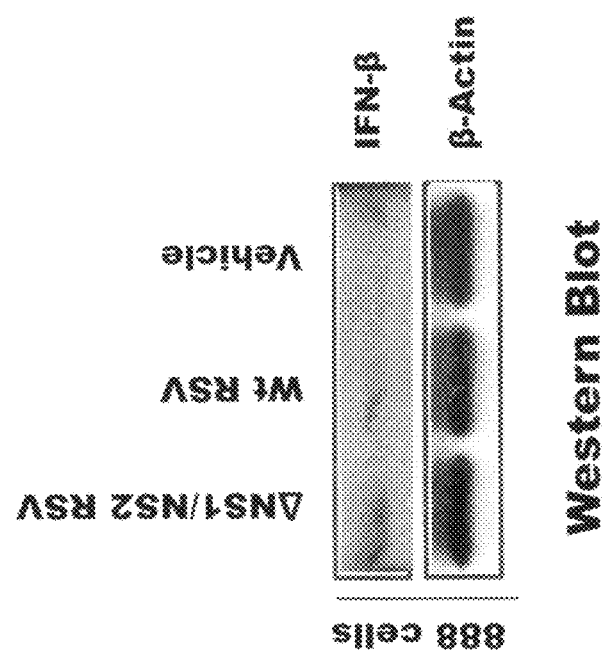

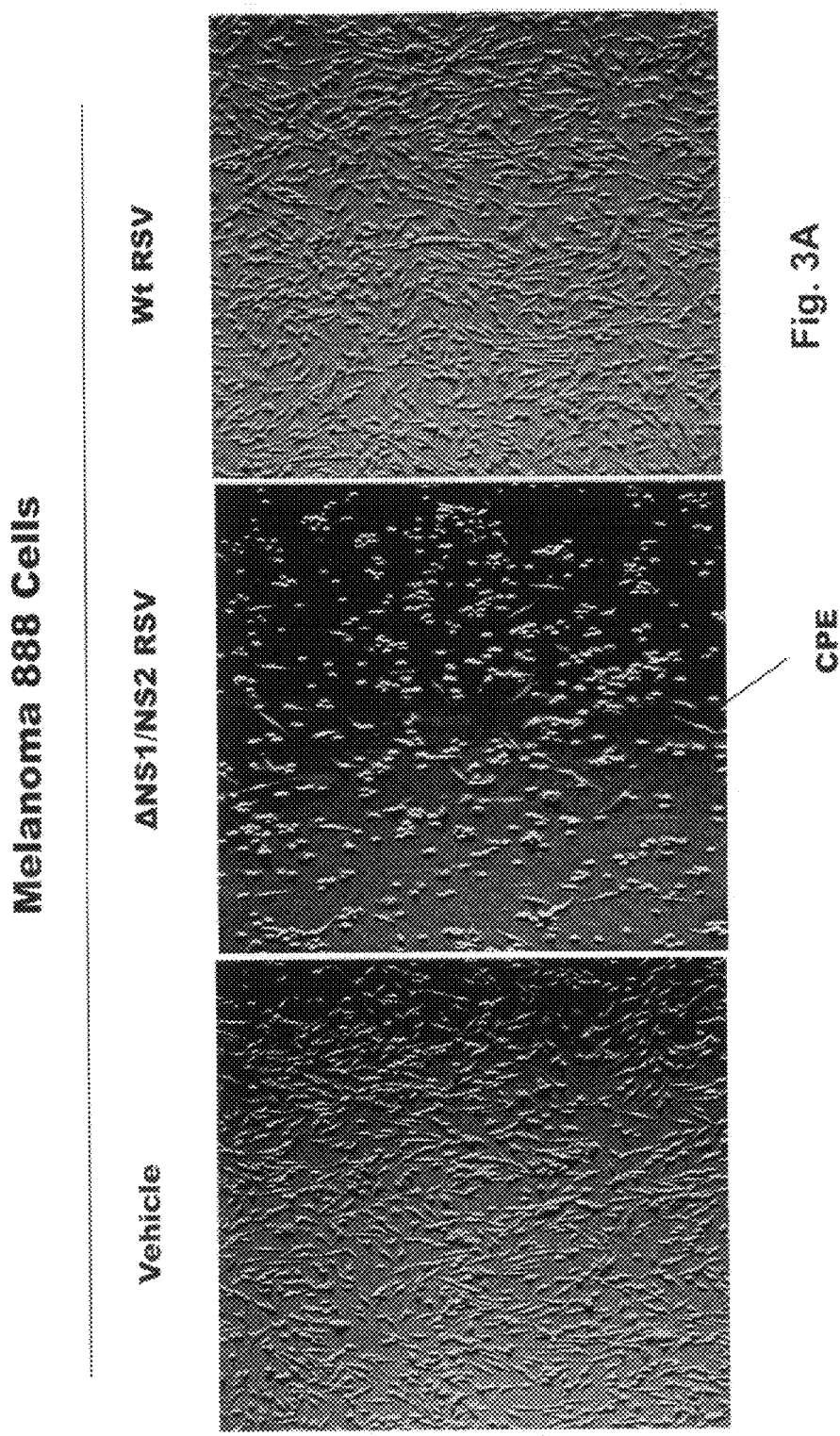

NS1/2-DEFICIENT RESPIRATORY SYNCYTIAL VIRUS AND MELANOMA TREATMENT

CROSS-REFERENCE TO RELATED APPLICATIONS

This application claims priority to U.S. provisional Application No. 61/398,236 filed on Jun. 22, 2010, the disclosures of which are incorporated herein in their entirety.

FIELD OF THE INVENTION

The invention is within the scope of oncolytic virotherapy. We used engineered respiratory syncytial virus (RSV) by deleting NS1 and NS2 gene, and found that the NS1/NS2 gene deficient RSV (ΔNS1/NS2 RSV), but not wild-type RSV (wt RSV), can specifically kill melanoma tumor cells, not normal human primary epidermal melanocytes.

BACKGROUND OF THE INVENTION

Melanoma: The incidence of melanoma is increasing worldwide. Despite decades of clinical research, patients with advanced melanoma continue to have a poor prognosis, and no agents have shown statistically significant improvement in overall survival in the patients with metastatic melanoma [1]. For patients with surgically resected, thick (≥2 mm) primary melanoma with or without regional lymph node metastases, the only effective adjuvant therapy is type I interferon [2]. Standard recommended therapy for patients with metastasis is single-agent dacarbazine, but responses to this agent and its oral analogue, temozolomide, are <15% and generally transient [3]. Biochemotherapy increases objective response rates but has not been shown to significantly improve survival compared with chemotherapy alone and is associated with additive toxicity [4]. Therefore, a safe and effective treatment remains a critical need.

Oncolytic virotherapy. Oncolytic virotherapy is a novel strategy using viruses, either naturally occurring or genetically modified, to selectively target and destroy tumor cells whilst leaving surrounding non-malignant cells unharmed [5]. The destruction of cancer cells occurs either through direct lytic rupture by multi-cycle viral replication or the subsequent induction of apoptosis [6] and successful application of virotherapy requires preferential and efficient amplification of the virus to lyse cancer cells. NS1/NS2 gene deficient RSV (ΔNS1/NS2 RSV) functions as an oncolytic virus killing melanoma tumor cells.

RSV biology. RSV belongs to the family Paramyxoviridae, subfamily Pneumovirinae, genus Pneumovirus. The viral RNA is approximately 15 kb in size and is flanked by a leader region at the 3' extremity of the genome and by a trailer region at the 5' extremity (FIG. 1). The viral genome contains individual genes for ten viral proteins [7]. The NS1 gene, unique to members of the genus Pneumovirus [8], is promoter-proximally located at the 3' end of the viral genome and its mRNA is the most abundant of the RSV transcripts in a linear start-stop-restart mode [9]. NS1 and NS2 are referred to as non-structural since they have not been detected in RSV particles. NS1 and NS2 are exclusively found in RSV-infected cells. Our group, along with others, has found that NS1 and NS2 can counter the type I IFN signaling during RSV infection [10, 11], implying that NS1 and NS2 play an important role in inhibiting the host's innate immune response.

RSV can be rendered nonpathogenic by mutating the NS1 and NS2 genes so that it no longer inhibits IFN release (FIG. 2), which attenuates viral infection in normal cells. However, these nonpathogenic RSV, ΔNS1/NS2 RSV, are still oncolytic (FIG. 3A) because tumor cells are defective in their ability to produce and respond to IFN and, therefore, efficiently support the propagation of ΔNS1/NS2 RSV. ΔNS1/NS2 RSV replicates to a high titer in melanoma cancer cells, compared to the normal primary epidermal melanocytes (FIG. 3B), and ΔNS1/NS2 RSV, not wt RSV, specifically kills melanoma cancer cells, but not normal human primary epidermal melanocytes PCS-200-013 cells (Table 1).

ΔNSI/NS2 RSV Induces Apoptosis in Human Melanoma Cancer Cells.

Evasion from apoptotic cell death unregulated cell proliferation and eventual tumor development is one of the hallmarks of oncogenic cell-transformation. We found that ΔNS1/NS2 RSV selectively induces apoptosis in tumor cells (FIG. 4A-B), and also generated cytopatheic effect (CPE) in melanoma cancer cells (FIG. 3A) as we demonstrated in our previous patent application U.S. 61/398,236, suggesting that multiply mechanism-mediated cell death participates in the anti-tumor effect of ΔNS1/NS2 RSV.

SUMMARY

This invention discloses a NS1/2 gene deficient-RSV (ΔNS1/NS2 RSV), which could be utilize to kill melanoma cancer cells. The RSV NS1 and NS2 proteins function as type-I-IFN antagonists, ΔNS1/NS2 RSV virotherapy produces more type-I-IFN, which prevents virus from replication in normal cells and also induces antitumor effects.

In another embodiment, the engineered virus could be any other virus having a similar gene as NS1 and NS2 genes, which functions as genes encoding the related proteins as type-I-IFN antagonists.

In another embodiment, the ΔNS1/NS2 RSV can be applied to kill melanoma cancer cells. Or the ΔNS1/NS2 RSV can be delivered to cancer spot through blood transfusion.

BRIEF DESCRIPTION OF THE FIGURES

FIG. 2. ΔNS1/NS2 RSV infection induces more type I IFN in human melanoma cells compared to wt RSV. Human melanoma cancer cells 888 were infected with indicated virus (MOI=10) and cell pellets were collected 20 hr post-infection and whole cell-lysates were immunoblotted using anti-IFN-β antibodies.

FIG. 3. Virus infection of prostate cancer cells. Morphology of virus-infected human melanoma 888 cancer cells 24 h post-infection. ΔNS1/NS2 RSV (MOI=10), not wt RSV, induced CPE in human 888 cells (FIG. 3A).

Table 1. Cytopathic effect (CPE) test showing ΔNS1/NS2 RSV selectively kills different types of melanoma cancer cells.

DETAILED DESCRIPTION OF THE INVENTION

ΔNS1/NS2 RSV preferentially kills melanoma cancer cells in vitro. Melanoma 888 cancer cells were infected with wt or ΔNS1/NS2 RSV (MOI=10). FIG. 3A shows that ΔNS1/NS2 RSV selectively induces CPE in 888 cells. Whereas, vehicle and wild type RSV has no effect on 888 cancer cells. As shown in Table 1, ΔNS1/NS2 RSV, but not wt RSV, preferentially kills 888, SK-MEL-3 and 624 melanoma cancer cells.

Figure 1:
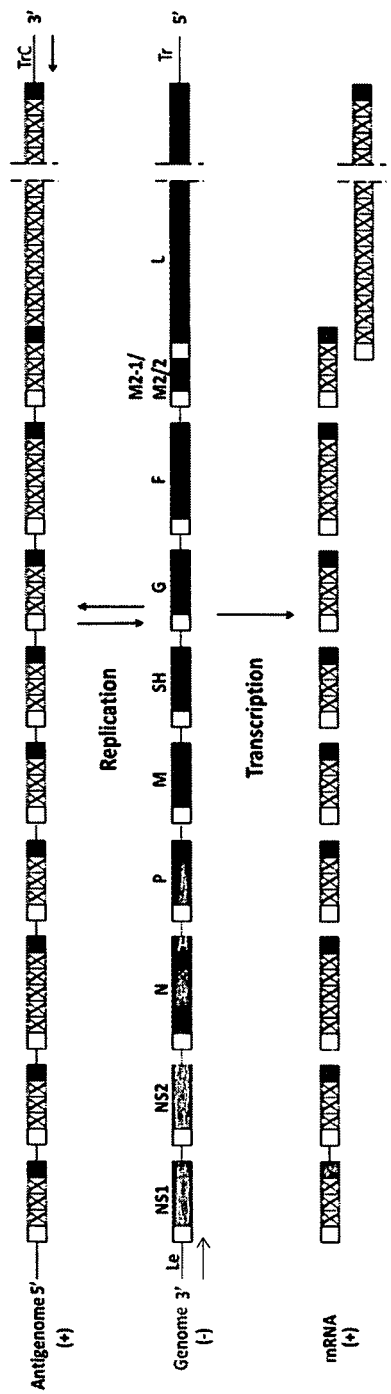
FIG. 1. Diagram of the RSV genome and its transcription and replication products. The virus genes are depicted as grey rectangles; the L gene, which comprises almost half of the genome, has been truncated. The GS and GE signals are shown as white and black boxes, respectively. The encoded anti-genome and mRNAs are indicated by hatched rectangles. Arrows indicate the location of the promoters.
Figure 3B:
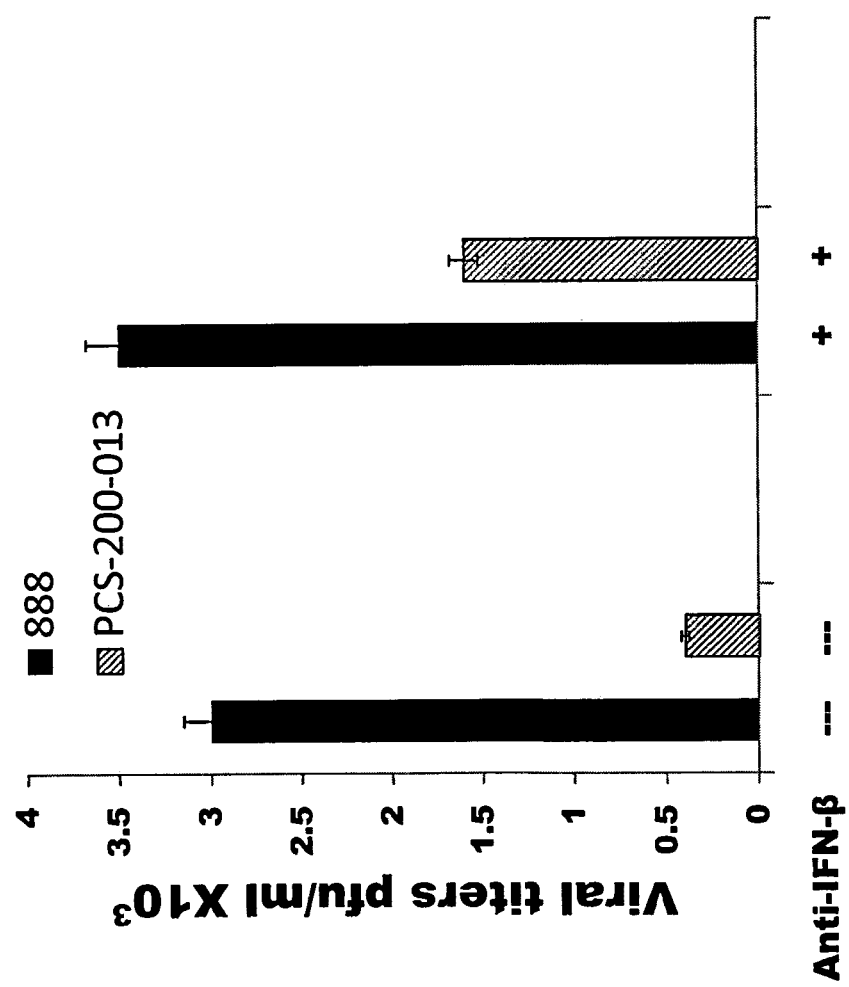
(FIG. 3B) 888 melanoma cancer cells were infected with viruses (MOI=10) and neutralizing Abs against IFN-β(2 μg/ml, ND50 is ~0.05-0.2 μg/ml PBL Interferon Source) were added 15 min post-infection, and viral titers were measured by plaque assay at 24 hr after infection. Standard deviations from three independent experiments are shown by the error bars.

ΔNS1/2 RSV infection induces more IFN-β in human melanoma cells compared to wt RSV (FIG. 2), but IFN does not significantly affect viral titers in melanoma 888 cells (FIG. 3B).

Figure 4A:
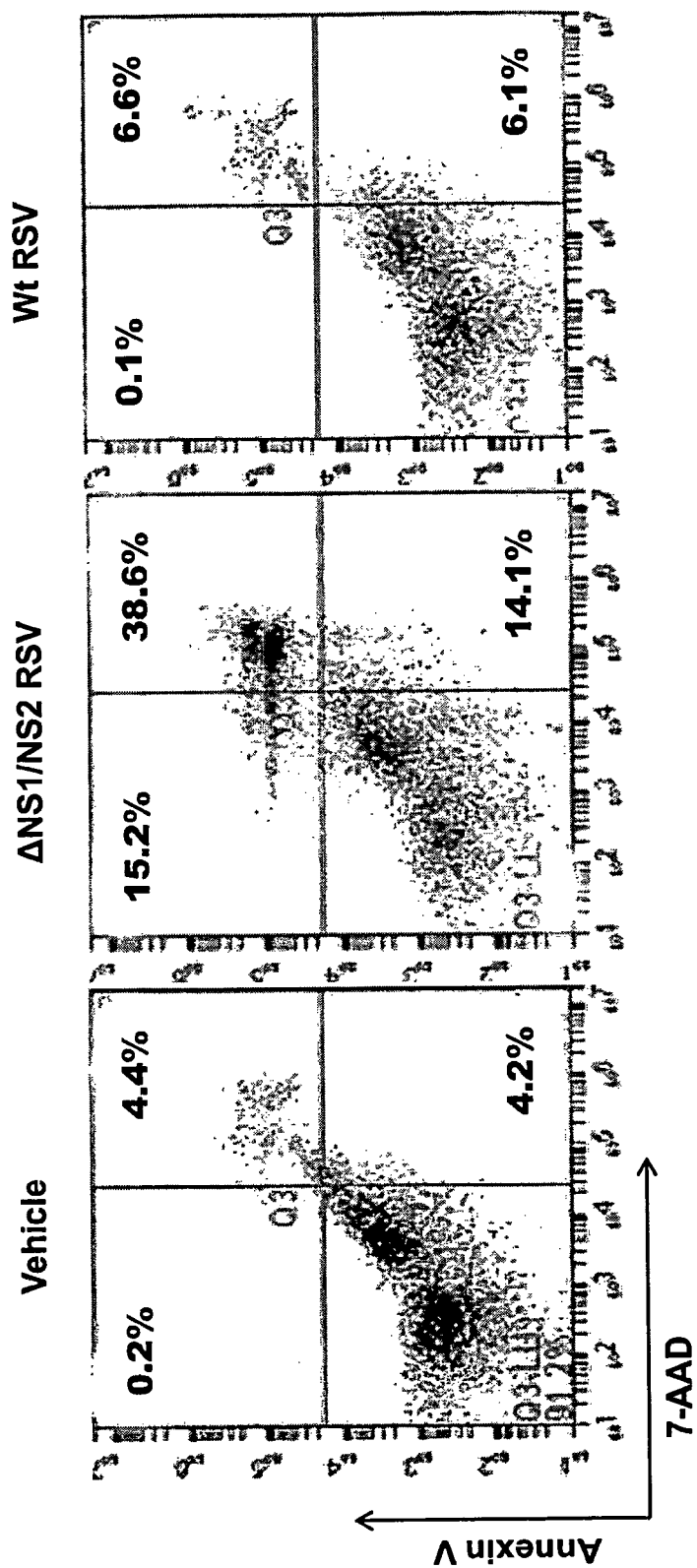
FIG. 4. ΔNS1/NS2 RSV infection induces apoptosis in melanoma cancer cells. Human melanoma 888 cells were infected with indicated viruses (MOI=10), and collected 24 h post-infection, respectively, cell apoptosis was analyzed using annexin V-binding and PI uptake assay (FIG. 4A).
(FIG. 4B) Verify virus-induced apoptosis in melanoma cancer cells by immunoblotting using indicated antibodies. Melanoma 888 cell-pellets were collected 24 h post-infection, and whole cell-lysates were immunoblotted.
Figure 4B:
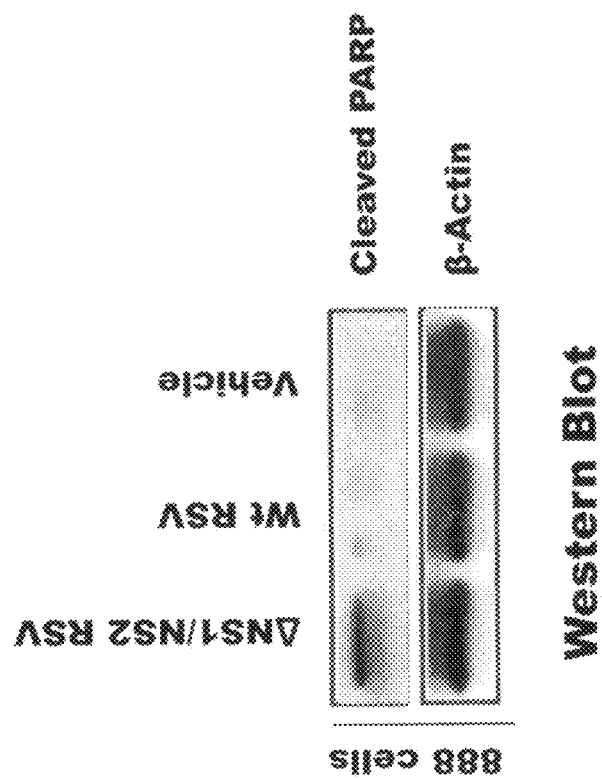

ΔNS1/NS2 RSV infection induces apoptosis in tumor cells. To test the differential effect of virus infection on apoptosis, 888 melanoma cancer cells were infected with the indicated viruses (MOI=10) and apoptosis was measured by the annexin V binding assay. FIG. 4A shows that ΔNS1/NS2 RSV selectively induces apoptosis in tumor cells, compared to the cell spontaneous apoptosis shown in controls, which was verified by immunoblotting (FIG. 4B), where apoptotic marker cleaved PARP was not observed in controls.

REFERENCE

1. Lens, M. B. and M. Dawes, *Global perspectives of contemporary epidemiological trends of cutaneous malignant melanoma.* Br J Dermatol, 2004. 150(2): p. 179-85.
2. Molife, R. and B. W. Hancock, *Adjuvant therapy of malignant melanoma.* Crit Rev Oncol Hematol, 2002. 44(1): p. 81-102.
3. Eggermont, A. M. and J. M. Kirkwood, *Re-evaluating the role of dacarbazine in metastatic melanoma: what have we learned in 30 years?* Eur J Cancer, 2004. 40(12): p. 1825-36.
4. Atkins, M. B., et al., *Phase III trial comparing concurrent biochemotherapy with cisplatin, vinblastine, dacarbazine, interleukin-2, and interferon alfa-2b with cisplatin, vinblastine, and dacarbazine alone in patients with metastatic malignant melanoma (E3695): a trial coordinated by the Eastern Cooperative Oncology Group.* J Clin Oncol, 2008. 26(35): p. 5748-54.
5. Parato, K. A., et al., *Recent progress in the battle between oncolytic viruses and tumours.* Nat Rev Cancer, 2005. 5(12): p. 965-76.
6. Berry, L. J., et al., *Potent oncolytic activity of human enteroviruses against human prostate cancer.* Prostate, 2008. 68(6): p. 577-87.
7. Collins, P. L., Y. T. Huang, and G. W. Wertz, *Identification of a tenth mRNA of respiratory syncytial virus and assignment of polypeptides to the 10 viral genes.* J Virol, 1984. 49(2): p. 572-8.
8. Hacking, D. and J. Hull, *Respiratory syncytial virus—viral biology and the host response.* J Infect, 2002. 45(1): p. 18-24.
9. Tran, K. C., P. L. Collins, and M. N. Teng, *Effects of altering the transcription termination signals of respiratory syncytial virus on viral gene expression and growth in vitro and in vivo.* J Virol, 2004. 78(2): p. 692-9.
10. Zhang, W., et al., *Inhibition of respiratory syncytial virus infection with intranasal siRNA nanoparticles targeting the viral NS1 gene.* Nat Med, 2005. 11(1): p. 56-62.
11. Spann, K. M., et al., *Suppression of the induction of alpha, beta, and lambda interferons by the NS1 and NS2 proteins of human respiratory syncytial virus in human epithelial cells and macrophages [corrected].* J Virol, 2004. 78(8): p. 4363-9

TABLE 1

ΔNS1/NS2 RSV selectively kills human melanoma cells

| Virus | CPE (hr post-infection) | | | |
|---|---|---|---|---|
| (MOI = 10) | 24hr | | 48hr | |
| Cells | ΔNS1/NS2 RSV | wt RSV | ΔNS1/NS2 RSV | wt RSV |
| PCS-200-013 (Human Primary Epidermal Melanocytes, Normal) | ---- | ---- | ---- | ---- |
| 888 | ++++ | ---- | NO | ---- |
| SK-MEL-3 | ++ | ---- | ++++ | ---- |
| 624 | ++ | ---- | ++++ | ---- |

Note:
−: no CPE;
++: CPE ≤ 50%;
++++: CPE ≥75%;
NO: not tested;

The invention claimed is:

1. A method to treat human melanoma cancer in a patient in need thereof comprising delivering an oncolytic ΔNS1/NS2 respiratory syncytial virus (RSV) to the patient wherein the RSV infects and causes oncolysis to thereby treat the patient.

2. The method of claim 1 wherein the RSV is suspended in saline and the RSV suspension is injected into cancerous tissue.

3. The method of claim 1 wherein the RSV is suspended in saline and the RSV suspension is injected intravenously.

4. The method of claim 1 wherein the RSV is suspended in medium and the RSV suspension is injected into cancerous tissue.

5. The method of claim 1 wherein the RSV is suspended in medium and the RSV suspension is injected intravenously.

* * * * *